United States Patent [19]

Calabrese

[11] Patent Number: 5,070,023
[45] Date of Patent: * Dec. 3, 1991

[54] AQUEOUS FERRIOXALATE COMPOSITIONS USEFUL AS CALIBRANTS

[75] Inventor: Gary S. Calabrese, North Andover, Mass.

[73] Assignee: Fisher Scientific Company, Pittsburgh, Pa.

[*] Notice: The portion of the term of this patent subsequent to Oct. 29, 2008 has been disclaimed.

[21] Appl. No.: 305,567

[22] Filed: Feb. 3, 1989

Related U.S. Application Data

[63] Continuation-in-part of Ser. No. 257,553, Oct. 14, 1988.

[51] Int. Cl.$^5$ ............................................. G01N 31/00
[52] U.S. Cl. .......................................... 436/8; 436/11; 436/19
[58] Field of Search ........................... 435/8–19; 423/594, 632, 415 R, 415 P; 252/408.1

[56] References Cited

U.S. PATENT DOCUMENTS

| | | | |
|---|---|---|---|
| 3,873,269 | 3/1975 | Kraffczyk et al. | 436/17 |
| 3,920,400 | 11/1975 | Scheibe et al. | 436/12 |
| 4,163,734 | 8/1979 | Sorensen et al. | 436/11 |
| 4,361,539 | 11/1982 | Weinberg et al. | 422/68 |
| 4,722,904 | 2/1988 | Feil | 436/11 |

OTHER PUBLICATIONS

*Photochemistry*, vol. 36, Vincze, pp. 289–296 (1987).
Hugh A. Taylor, "Analytical Methods and Techniques for Actinometry", Analytical Photochemical Analysis (1971, J. M. Fitzgerald, ed. pp. 91–115).
L. Vincze & S. Papp, "Individual Quantum Yields of . . .", J. of Photochemistry, vol. 36 (1987), pp. 289–296.
C. G. Hatchard & C. A. Parker, "A New Sensitive Actinometer", Proc. Roy. Soc. (London), vol. A235, pp. 518–536 (1956).
C. A. Parker, "Induced Antoxidation of Oxalate . . . ", Trans. Faraday Soc., vol. 50, pp. 1213–1221 (1954).
C. A. Parker & C. G. Hatchard, "Photodecomposition of Complex Oxalates", J. Phys. Chem. vol. 63, pp. 22–26 (1959).

*Primary Examiner*—David L. Lacey
*Assistant Examiner*—William K. Y. Chan
*Attorney, Agent, or Firm*—Alan M. Doernberg

[57] ABSTRACT

Aqueous acidic ferrioxalate compositions are disclosed for use as calibrants of pCO2 and of PO2 after photodecomposition. Compositions with high iron(III) to oxalate molar ratios (e.g., 5:1 to 100:1 with 0.3 to 15 millimolar oxalate) produce carbon dioxide on exposure without oxygen consumption. Compositions with low iron(III) to oxalate ratios (e.g., 1:100 to 1:2000) with 0.1 to 5 millimolar iron(III) produce carbon dioxide on exposure with concurrent oxygen consumption. Use of the two types of compositions enables calibration values to be established with varying pCO2 values and with, respectively, high and low pO2 values.

19 Claims, 3 Drawing Sheets

AQUEOUS FERRIOXALATE COMPOSITIONS USEFUL AS CALIBRANTS

This is a continuation-in-part of commonly-assigned and copending U.S. Ser. No. 257,553, filed Oct. 14, 1988.

The present invention relates to acidic compositions containing ferrioxalate useful as calibrants in measuring the partial pressure of carbon dioxide or of oxygen in an aqueous sample liquid (e.g., blood).

Partial pressures of normally volatile components in liquids are frequently measured. For example, partial pressures of oxygen, of carbon dioxide or of both are measured in fermentation, in enviromental analysis, in clinical diagnosis and in a variety of other contexts. One of the most developed contexts for such analyses is in the measurement of pH along with the partial pressures of oxygen and of carbon dioxide in arterial or venous blood (a field generally referred to as blood gas analysis).

While the instruments for making such measurements are of many designs, a prototypical instrument is the Instrumentation Laboratory 1312 blood gas instrument sold by the present assignee Fisher Scientific Company. The sensing portion of such instruments is described in U.S. Pat. Nos. 4,361,539 and 4,361,540, each issued Nov. 30, 1982, and 4,443,407, Apr. 17, 1984, each of Weinberg and Cormier and currently assigned to Fisher Scientific Company. Such instrument has a series of sensing electrodes in series: a Clark oxygen electrode, a Severinghaus carbon dioxide electrode, a pH sensing electrode and a reference electrode (for the pH electrode).

Such instrument may be calibrated with one or more calibrants of known pH, pCO2 and pO2 values prior to each sensing measurement, and may be calibrated with two calibrants upon start-up and periodically thereafter (or when the measurement of quality control liquids indicates that the instrument is out of calibration). Such one-point calibration after each sensing measurement is described in U.S. Pat. No. 4,039,933 to Moran (Aug. 2, 1977).

In performing such calibration, it is conventional to use liquid buffers for the pH measurement and humidified gases for the pCO2 and pO2 measurements. For example, as described at col. 8, lines 22-35 of U.S. Pat. No. 4,361,539, calibration gas can be bubbled through a bubble chamber and then the liquid flowed past the ports having the pCO2 and pO2 electrodes. Using the circuitry of U.S. Pat. No. 4,039,933, the voltage registered at the pCO2 electrode and the amperage measured at the Clark oxygen electrode can be used to generate a compensatory voltage in the circuitry of U.S. Pat. No. 4,039,933.

The use of such gas mixtures in the calibration of blood gas instruments has led to the requirement that bulky gas tanks be present in close proximity to the blood gas instrument. Such tanks are often cumbersome in locations where blood gas measurements are made: in cardiac care, respiratory care and operating room areas of hospitals; and in some enviroments, such gas mixtures are unavailable. The elimination of such tanks would facilitate moving the blood gas instrument closer to where the blood is drawn.

The use of calibration liquids, including flourocarbon emulsions, having defined values of pH, pCO2 and pO2, have been proposed in a number of patents, including U.S. Pat. Nos. 4,722,904 to Feil (1988) and 4,151,108 and 4,163,734 to Sorenson (1979), but such compositions have been used commercially only as quality control materials, and not for calibration of the instrument. See also Hitachi's Kokai 61/22246 (Jan. 30, 1986).

Acidic aqueous ferrioxalate compositions have been developed for the field of actinometry. Typically, a recrystallized ferrioxalate salt, such as the sodium or potassium salt, is dissolved in water with an acid added to lower the pH to 1 or 2. Such compositions inherently have a 3:1 molar ratio of oxalate to iron (III). Since the purpose of such compositions in actinometry is to quantitate a light source, excess ferrioxalate (6 millimoles per liter or more) is provided in order that photons can maximally cause the photoreaction in which iron (III) is reduced to iron (II). A developer solution (e.g., o-phenanthrone monohydrate) is combined with the solution after exposure to quantitate the iron (II) produced. No use is made of the carbon dioxide produced by ferrioxalate decomposition. See H. A. Taylor, Analytical Methods and Techniques for Actinometry, pages 91-115 (esp. 94-97 and 109-111), in Analytical Photochemistry and Photochemical Analysis (1971, T. M. Fitzgerald, ed.); C. G. Hatchard et al, Proc. Royal Soc. (London), Vol. A235, pp. 518-536 (1956); C. A. Parker, Trans. Faraday Soc. vol. 50, pp. 1213-21 (1954).

In elucidating the mechanisms and physical chemistry of the photodecomposition of ferrioxalate, factors such as pH, oxalate concentration and iron (III) concentration have been varied. See L. Vincze and S. Papp, J. of Photochemistry, vol. 36, pp. 289-296(1987). Noteworthy are the compositions of Table 5 on page 294 which employ varying amounts of recrystallized potassium ferrioxalate of concentration as low as 0.4 mM and the compositions of Table 2 page 292 wherein iron (III) is 0.198 or 0.18 mM, oxalate is varied from 0.01 mM to 10 mM and sulfuric acid is varied from 0.01M to 0.50M. Various properties of these solutions, including pH, are shown in Table 2.

BRIEF DESCRIPTION OF THE INVENTION

The aqueous compositions of the present invention represent acidic ferrioxalate solutions which, on photodecomposition, yield carbon dioxide partial pressures in a range useful for calibration of the measurement of carbon dioxide. The compositions are of two types:
(A) those with a stoichiometric excess of iron (III) over oxalate [less than a 3:1 molar ratio of oxalate to iron (III)] and
(B) those with a stoichiometric excess of oxalate relative to iron (III) [more than a 3:1 molar ratio of oxalate to iron (III)].

The compositions are further optimized for speed of the photodecomposition reaction and stability in the absence of light.

Thus, a first form of the present invention provides an aqueous solution having a pH of 0 to 5 and comprising 0.3 to 15 millimoles per liter oxalate and 1.5 to 200 millimoles per liter of iron(III); the molar ratio of iron-(III) to oxalate being 5:1 to 100:1. Because such compositions have an excess of iron(III) over the molar ratio for ferrioxalate (1:3), they do not produce a reduction in oxygen partial pressure upon photodecomposition.

A second form of the present invention provides an aqueous solution having a pH of 0 to 5 and comprising 0.2 to 5 millimoles per liter iron(III) and at least 1 millimole per liter oxalate: the molar ratio of oxalate to iron(III) being at least about 5:1.

A third form of the present invention provides an aqueous solution having a pH of 0 to 5 and comprising 0.1 to 5 millimoles per liter of iron(III) and at least 10 milliomoles per liter of oxalate; the molar ratio of oxalate to iron(III) being at least about 100:1.

In both the second and third forms of the invention, oxalate is present in excess of the 3:1 molar ratio. In such cases, it has been found that photodecomposition leads to a consumption of oxygen and thus a reduction in oxygen partial pressure of reproducible amounts. Thus, employing a composition of the latter type as one calibrant and one of the former type as another calibrant, calibration at two levels of oxygen partial pressure and at two levels at carbon dioxide partial pressure can be achieved even though both composition have identical gas partial pressures before photodecomposition.

DETAILED DESCRIPTION OF THE INVENTION

The calibration liquids of the present invention contain ferrioxalate as a precursor of the gas carbon dioxide in a defined amount. The composition and amount (concentration) of ferrioxalate is designed to yield, upon essentially complete photochemical conversion the gas, a partial pressure of carbon dioxide in a range useful for calibration of an instrument to measure that gas. Such precursor concentration is, in general, lower than would be the concentration of the same precursor in a liquid used to quantify the intensity of a light source. Ferrioxalate, in its unexcited form, can be represented by the formula:

and can be formed by mixing oxalate salts (typically the sodium or potassium salt) with iron(III) salts such as ferric chloride or ferric ammonium sulfate. Depending upon the pH, the ratio of Fe(III) to oxalate and their absolute concentrations, a number of species having, for each iron(III), one, two or three oxalates (and a charge of $+1$, $-1$ or $-3$, respectively) are believed to exist and to yield carbon dioxide upon exposure to light.

For reasons discussed below, the preferred total concentration of ferrioxalate in the calibration liquid for use with a blood gas instrument is about 0.1 to 5 millimoles per liter, especially about 0.2 to 2 millimoles per liter. Concentrations in that narrow range or higher, such as up to 5 millimoles per liter, may be used for calibrating other instruments that measure $pCO_2$.

Other constituents of the calibration liquid are preferably adjusted in order to facilitate to conversion of the precursor to the gas (i.e., ferrioxalate to carbon dioxide) when intentionally exposed to light for that purpose, but to minimize any other decomposition of the precursor (especially thermally). In the case of ferrioxalate, it is therefore preferred that the calibration liquid be aqueous and have an acidic pH in the range of about 0 to about 5 (preferably about 0 to about 3, especially about 0 to about 2). If the pH of the aqueous solution is too high, the rate of thermal decomposition of the ferrioxalate may be unacceptably high. If the pH of the aqueous solution is too low, a proportion of the oxalate anions may be protonated and, in that form, too difficult to photooxidize.

In the case of ferrioxalate precursor liquids, the mechanism of photochemical decomposition permits two types of overall compositions: on in which the main follow-up reaction to the primary photoreaction is the reduction of iron from valence three to valence two, and another in which the reduction of oxygen occurs. These two types of compositions can be appreciated by realizing that ferrioxalate complex ions are normally formed by separate introduction of oxalate anions and iron (III) cations into the solution. Molar ratios of iron-(III) to oxalate can be chosen such that one ingredient or the other will be the limiting reagent. Thus, if high iron(III) to oxalate ratios (e.g., 5:1 to 100:1, especially 10:1 to 50:1) are used, oxalate will be the limiting reagent, and the solution will contain hexaaqua iron (III) cations in a pH-dependent equilibrium with various iron(III) hydrolysis products in addition to the ferrioxalate complex anions.

There are various theories about which complexes of iron(III) and oxalate are converted by light to an initial, unstable reaction intermediate. Nevertheless, if iron(III) is present in excess, then the next reaction would be expected to be between that intermediate and another iron(III) species, to produce carbon dioxide and iron-(II). The experimental data supports the premise that such a mechanism that does not deplete oxygen is the primary mechanism for solutions having a stoichiometric excess of iron(III) over oxalate.

When iron(III) is present in near stoichiometric amounts or less, then the next reaction could also be between that intermediate and oxygen (dioxygen), if present, to form carbon dioxide and a reduced form of oxygen. The experimental data supports the premise that reaction of the intermediate with oxygen occurs to a sufficient extent such that oxygen is depleted; and the significant occurrence of such a reaction is the primary mechanism for solutions having a near stoichiometric amount or excess of oxalate over iron(III) (e.g., those with a molar ratio of oxalate to iron(III) of at least 5:1, preferably at least 100:1 and especially about 100:1 to about 2000:1.)

Based upon the above reasoning, an exemplary recipe for a calibration solution having an excess of oxalate would be:

potassium oxalate monohydrate (80 mmol/L)
ferric ammonium sulfate dodecahydrate (0.20 mmol/L)
sulfuric acid (0.05 mol/L)

and an exemplary recipe for a calibration solution having an excess of iron(III) would be:

potassium oxalate monohydrate (0.75 mmol/L)
ferric ammonium sulfate dodecahydrate (15.0 mmol/L)
sulfuric acid (0.05 mol/L).

In each case, the balance is distilled deionized water. Suitable recipes can be established from the above for other oxalate sources (e.g., oxalic acid, sodium oxalate), other iron(III) sources (e.g., ferric chloride, ferric sulfate) or other acidifying consituents (e.g., hydrochloric acid).

The present use of ferrioxalate contrasts with its use in actinometry. In that field, the ferrioxalate is provided in acidic solution at high concentration, generally with a molar concentration of ferrioxalate of 0.006 moles/liter up to 0.15 moles per liter. As indicated in the chapter by Hugh A. Taylor entitled "Analytical Methods And Techniques For Actinometry" in *Analytical Photochemical Analysis* (J. M. Fitzgerald, ed., 1971), such actinometers may employ potassium ferrioxalate which has been precipitated and recrystallized (and thus contains neither access oxalate nor excess iron (III). Solutions of the potassium ferrioxalate are exposed to light of the unknown intensity, and then the exposed solution is combined with a developer solution of o-phenanthroline monohydrate in water. Ferrous ions produced as a by-product of the the ferroixalate decomposition react quantitatively with the chromagen to form a chromophore, that can be quantitated. It should thus be appreciated that, in such reaction, oxalate must not be in excess (or else the reduction of iron(III) to iron(II) will not be quantitative) and no use is made of the carbon dioxide product of ferrioxalate decomposition.

By contrast, the present solutions should normally correspond to 0.1 to 5 mM ferrioxalate, yielding about 8 mm Hg pCO2 to about 600 mm Hg pCO2, respectively. With iron(III) at stoichiometric amounts or more, this corresponds to 0.3 to 15 mM oxalate. With oxalate in excess, this corresponds to 0.1 to 5 mM iron(III).

Especially for blood gas instrument calibration, preferred ranges are those yielding pCO2 values of 30 to 75. This corresponds generally to 0.2 to 0.5 mM iron-(III) if oxalate is in excess and 0.6 to 1.5 mM oxalate if iron is in excess. Precise proportions to achieve a particular pCO2 value can be determined through routine experiments.

Oxalate can exceed 15 mM concentration without yielding more than 5 mM ferrioxalate (and thus more than 600 mm Hg pCO2), provided that iron (III) concentration does not exceed 5 mM. In such cases oxalate may be present up to its solubility limits (see Example 12, below). Excessive iron (III) levels, such as over 200 mM, are not desirable because of the light absorption by the excess iron (III).

In the first form of the present invention, iron(III) is in stoichiometric excess with the molar ratio of iron(III) to oxalate being 5:1 to 100:1 compared to the stoichiometric ratio of 1:3. Examples are given below with molar ratio of 10:1, 20:1, 50:1 and 100:1, In each such case, the oxygen partial pressure is reduced minimally (10% or less) in the course of the photodecomposition. By contrast, with a 1:1 molar ratio, oxygen partial pressure is substantially reduced (85% in one case) even though there is a threefold molar excess of iron (III). Accordingly, the preferred molar ratio in such cases is 10:1 to 50:1. To achieve the preferred ferrioxalate range of 0.2 to 0.5 mM, the oxalate concentrate should be 0.6 to 1.5 mM. That corresponds to iron(III) being 3 mM to 150 mM for the broad molar range (5:1 to 100:1) and 6 mM to 75 mM for to narrow molar range (10 to 75 mM). By contrast, the iron(III) rich composition of Table 2 of the Vincze and Papp article have only 0.198 or 0.18 mM iron(III) and 0.01 or 0.1 mM oxalate.

In the second form of the invention, oxalate is in molar excess [at least at 5:1 molar of oxalate to iron(III)] and iron(III) is present at 0.2 to 5 mM, preferably 0.2 to 0.5 mM. The oxalate-rich compositions of Table 2 of Vincze and Papp have only 0.198 or 0.18 mM oxalate.

The molar ratio in such cases is preferably at least 100:1, more preferably 100:1 to 2000:1 and especially 300:1 to 1000:1. The preference for higher oxalate:iron-(III) ratio is based upon an increased photodecomposition rate as one goes from 1:1 to 5:1 to 10:1 to 100:1 to 200:1 to 400:1. See example 34 and Table IX. The preference to avoid excessive oxalate amounts (over 4000:1 or 2000:1) is to avoid expense and to avoid possible precipitation of oxalate salts under some storage conditions.

The pH of such solutions can be 0 to 5, but is preferably 0 to 2 and more preferably 1.0 to 1.5. The iron(III) concentration is 0.2 to 5 mM, preferably 0.2 to 0.5 mM and more preferably 0.2 to 0.25 mM. Such amounts yield carbon dioxide partial pressure in a range (35 torr and higher) particularly useful for calibrating blood gas instruments.

In the third form of the invention, oxalate is at substantial molar excess to iron (at least 100:1) and iron is present at 0.1to 5 mM concentration. Such high excesses of oxalate yield a rapid photodecomposition reaction and a rapid depletion of oxygen partial pressure. As in the second form of the invention, pH is preferably 0 to 2 (especially 1.0 to 1.5) and iron(III) is preferably 0.1 to 0.5 mM (especially 0.20 to 0.25 mM). The molar ratio is preferably 100:1 to 2000:1, especially 300:1 to 1000:1.

The present calibration solutions are preferably stored under conditions that do not promote decomposition. In the case of the preferred ferrioxalate solutions, this generally means storage at room temperature or below, and shielding from light, especially light of 500 nm wavelength or less (blue or near-ultraviolet light). Nevertheless, provided that proper pH is maintained, brief exposures to temperatures of up to 50 C. are not deleterious, and shielding in dark glass or plastic bottles is usually adequate.

For use, an aliquot of the calibrator solution is exposed to light of sufficient wavelength and intensity to decompose the precursor essentially completely. For ferrioxalate, the present examples show that, in general, carbon dioxide formed reaches a plateau at which small variations of exposure level (variations in irradiation time less than 10 seconds) do not cause significant changes (more than 2%) in carbon dioxide partial pressure.

Thus, upon such exposure (typically with blue or near-ultraviolet light for ferrioxalate) a reproducible amount of carbon dioxide gas is generated (measured, for example, in millimodes per liter). So long as the temperature and pressure of the liquid is reproducible when that liquid is introduced into the instrument at the measuring electrodes (e.g., the Severinghaus carbon dioxide electrode), such reproducible carbon dioxide concentration will translate into a reproducible carbon dioxide partial pressure. Furthermore, if the instrument produces a reproducible temperature at the measuring electrode (e.g., 37 C.) and the barometric pressure is measured, any changes in pressure will have a direct and calculable effect upon the partial pressure of carbon dioxide that either can be compensated for, to calibrate the electrode to an "actual" partial pressure of carbon dioxide, or can be left uncompensated to cancel out the same effect on the sample. Thus, if the barometric pressure is slighlty below standard conditions (one atmosphere pressure at sea level), the carbon dioxide partial pressure of the exposed calibrant will be measured at a value slightly below what it would have been at standard conditions. That variation could either be compensated for electronically or could be left alone to adjust for the same difference in the carbon dioxide partial pressure of the sample, which would also have a slightly lowered value at the slightly depressed barometric pressure compared to measurement of the same sample under standard conditions.

While the volume of the aliquot of sample that is exposed can be controlled somewhat accurately, it is not necessary for this volume to be precisely controlled. This is because it is the concentration of carbon dioxide produced (measured, e.g., in mmol/l) rather than the amount of carbon dioxide produced (measured, e.g., in mmol) that correlates with the measured partial pressure. It is only necessary that the exposed aliquot be large enough to flush the chamber near the measuring electrode of any residual sample or buffer, and yield the reproducible $pCO_2$ value unaffected by the $pCO_2$ of any liquid that preceded it.

The conveying of the exposed aliquot of calibration liquid to the vicinity of the measuring electrode can occur by any conventional pumping or drawing technique. There is no effect of light on the exposed aliquot. It is important, however, that the exposed aliquot be prevented from gas exchange with any other liquid or gas between the time of exposure and the time of measurement.

Figure 1:
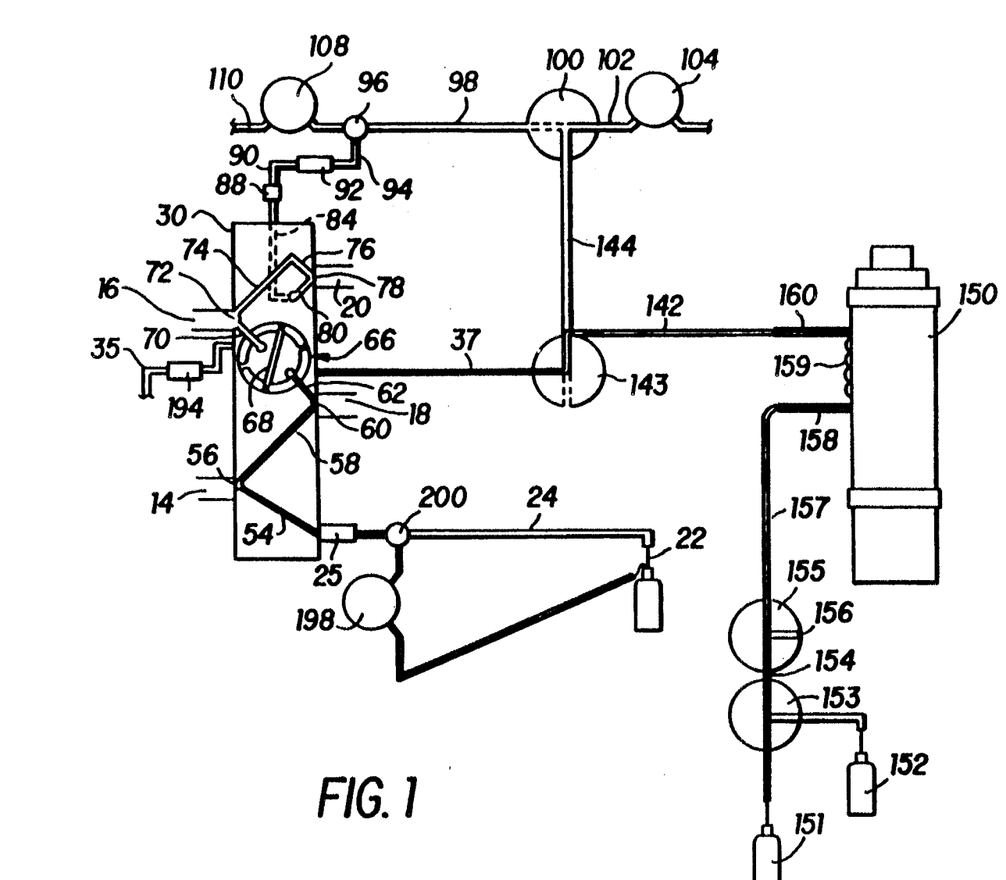
FIG. 1 is schematic view of an apparatus for using the compositions of the present invention showing the overall relationship between the calibrator liquid storage vessel, the exposure device and the electrode assembly.
Figure 3:
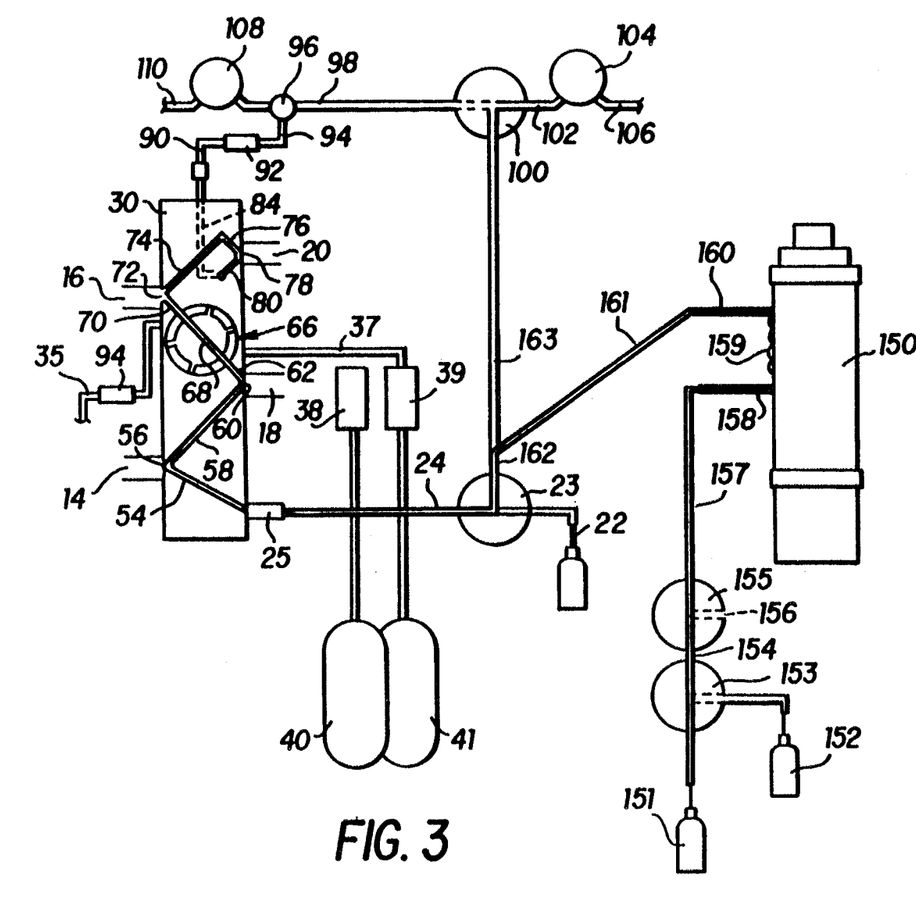
FIG. 3 is a schematic view of a test fixture used in conjunction with a Model 1312 Instrumentation Laboratory blood gas analyzer to demonstrate the use of the present compositions.

The examples and description of FIGS. 1 and 3 in parent U.S. Ser. No. 257,553, filed Oct. 14, 1988, illustrate how the exposed aliquot can be brought into contact with the measuring electrode either along a sample pathway or along a calibrant pathway. The former is somewhat less preferred for ferrioxalate solutions in that, if the acidic exposed aliquot is brought into contact with a pH electrode (as would normally be the case in a sample pathway), the environment of the pH electrode becomes unusually acidic and must be flushed with liquids to bring it back to the desired range (e.g., to pH 7.0 to 7.6 for blood). As indicated at col. 7, lines 29–41 and col. 8, lines 22–31 of U.S. Pat. No. 4,361,539, a calibration pathway can be used instead that will bring the exposed calibrant into contact with the Clark oxygen electrode and with the Severinghaus carbon dioxide electrode, but not in contact with the pH electrode. Such disclosures are incorporated herein by reference.

It is often desirable that each composition before photodecomposition have a $pO_2$ of known value, as by tonometry with room air. So long as the barometric pressure is known and temperature is controlled or known, the $pO_2$ that results from such tonometry (liquid-gas equilibration) will be reproducible. The resultant $pCO_2$ of the tonometered and unexposed liquid will also be reproducible, and essentially zero. Exposure of an aliquot of the liquid after such tonometry will cause the increase of the $pCO_2$ value by a known amount, as described above. If the solution is one leading to carbon dioxide formation without oxygen consumption (i.e., a ferrioxalate solution with excess iron (III)), then the exposed calibrant will retain the $pO_2$ value established on tonometry. If the solution is of a composition leading to ferrioxalate decomposition accompanied by oxygen consumption, then the $pO_2$ value will be depressed from the value established on tonometry by a reproducible amount. It should be appreciated that, if two calibrant solutions are used of the two different types (one having a stoichiometric excess of iron (III), the other having a stoichiometric excess of oxalate), then the liquids introduced into the measuring chambers after tonometry and exposure can be made to differ in a reproducible fashion in both $pO_2$ and $pCO_2$. This enables two liquids to be used to calibrate both electrodes at two values without any gas besides air being used.

Calibration of either or both electrodes at two values can be performed intermittently (e.g., at the start of each eight-hour shift and whenever control values show a need for recalibration) by exposing one calibrant, measuring and comparing to stored values, washing the electrodes, exposing the other calibrant, measuring and then comparing to other stored values. Such a two-point calibration differs from what is conventional in that each final calibrant is a liquid phase and has been generated by light exposure (or tonometry followed by light exposure) rather than by using humidified gas mixtures. Thus, the calibration medium (gases dissolved in an aqueous solution) more closely resembles the samples (e.g., whole blood), which are liquids. A one-point calibration can be performed either immediately before or immediately after measurement of values on each sample (conventionally the one-point calibration is performed before the sample measurement so that final values can be reported immediately after the measurement on the sample).

Referring now to FIG. 1, an apparatus is shown in schematic form, for calibrating a blood gas instrument. The flow cell 30 shown in FIG. 1 is described in detail in U.S. Pat. Nos. 4,443,407 and 4,361,539, which should be consulted for mechanical and other details of the arrangement of electrodes, inlets, outlets and temperature control devices. Two alternate sample inlets 22a and 22b are each connected to valve 23 for alternate connection to sample line 24. Sample line 24 is connected to flow cell 30 through sample preheater 25 (shown as preheater 130 in the Figures of U.S. Pats. Nos. 4,443,407 and 4,361,539).

Four electrodes are each connected to flow cell 30 by insertion in sleeves through heat blocks on either side of flow cell 30 as shown in FIGS. 3 and 10A of U.S. Pat. No. 4,361,539. The $pO_2$ electrode 14 terminates at sensor port 56 in flow cell 30. The pH sensing electrode 16 terminates at sensor port 72 in flow cell 30. The $pCO_2$ electrode 18 terminates at sensor port 60 in flow cell 30. The pH reference electrode 20 terminates at sensor port 78 in flow cell 30.

A flow control valve 66 is provided in flow cell 30, and is adjustable between three operative positions as is described in more detail in U.S. Pat. No. 4,361,539. One of the calibrating positions is illustrated in FIG. 15 of that patent and in present FIG. 1. Another of the calibrating positions is described at col 8, lines 23-31 of that patent. The analysis position is illustrated in FIGS. 10A and 11 of that patent and in present FIG. 3. In that analysis position, sample line 24 is connected to position sensor 88 by a pathway comprising first leg 54, second leg 58, third leg 62, transverse passage 68 through valve 66, fourth leg 70, fifth leg 74, sixth leg 76, seventh leg 80 and outlet passage 84. As described more fully in the prior patents, a blood sample is conveyed by the instrument in the analysis position past sensor ports 56, 60, 72 and 78, so that the sample can be measured by electrodes 14, 16, 18 and 20 in a fashion which is now conventional in the blood gas field. Position sensor 88 (illustrative of the several position sensors described at col. 7, lines 7–25, of U.S. Pat. No. 4,361,539) can be considered the top (downstream) end of the sample analysis region.

In the calibration position shown in FIG. 1, valve 66 has been turned so that transverse passage 68 communicates with neither third leg 62 nor fourth leg 70. Instead, a first buffer solution in line 35 is connected through buffer preheater 194 to a passage in valve 66 not shown in the present Figures (but indicated as 88b in U.S. Pat. No. 4,361,539). That passage connects line 35 to fourth leg 70 so that buffer can be drawn into fourth leg 70, fifth leg 74, sixth leg 76 and seventh leg 80 so as to be in contact with pH sensing electrode 16 at sensing port 72 and in contact with pH reference electrode 20 at sensing port 78 and to form an electrical connection therebetween. Measurement of the voltage difference between electrodes 16 and 20 is used to calibrate the pH measurement in a conventional fashion.

Also in the calibration position shown in FIG. 1, a calibrant line 37 is connected through a passage in valve 66 to second leg 62. Such connection within valve 66 is shown as passage 88a in U.S. Pat. No. 4,361,539. Whereas, in the prior art devices, the calibrant line is connected to a bubble chamber, in the present system, it is connected to an irradiation chamber as described more fully below.

Other aspects of the conventional portion of the system of FIG. 1 are described in U.S. Ser. No. 257,553.

The calibrant is prepared for introduction into legs 62, 58 and 54 of flow cell 30 through calibrant line 37. Two reservoirs of calibration liquid 151 and 152 are each connected to a selector valve 153. Selector valve 153 can connect either reservoir to one inlet 154 of intake valve 155. Intake valve 155 can connect either selector valve 153 or a connection to room air via line 156 to an inlet line 157.

A tonometer device such as a device which passes the liquid past a gas-permeable membrane or which bubbles air through the liquid may be located along inlet line 157. Alternatively, such equilibration with room air may occur in containers 151 and 152. The pressure and temperature at the time of such equilibration should preferably be carefully controlled to have a consistent value or, if not so controlled, then should be carefully measured so as to be compensated for.

Inlet line 157 is connected through an uncovered glass tube inlet portion 158 of irradiation device 150 to the coil portion 159 of irradiation device 150. The coil portion 159 is connected at its opposite end to an outlet line 142 (which includes uncovered glass tube outlet portion 160 of irradiation device 150) to a branch point with line 144 near one inlet to valve 143.

To expose an aliquot of the calibration liquid in reservoir 151, valves 153 and 155 are positioned to connect reservoir 151 to line 157. Simultaneously, valves 100 and 143 are positioned to connect line 144 to line 102 and aspiration pump 104, but to disconnect line 144 from line 37. Operation of aspiration pump 104 in this position will draw calibration liquid from reservoir 151 into coil portion 159 of irradiation device 150. Upon activation of the light source in irradiation device 150, as described below, essentially complete photochemical reaction will occur on the aliquot of calibration liquid which is then in coil portion 159.

Depending upon the relative volumes of liquid in coil portion 159 and drawn therefrom by aspiration pump 104, the aliquot of calibration liquid in line 142 may either be exposed or unexposed.

Upon completion of irradiation, valves 100, 143 and 66 are adjusted to connect line 142 through line 37 to legs 62, 58 and 54 in the serpentine flow path through flow cell 30. Pump 198 can then draw calibration liquid from coil portion 159 through lines 142 and 37 into the serpentine flow path in contact with pCO2 electrode at sensor port 60 and in contact with pO2 electrode at sensor port 56.

Figure 2:
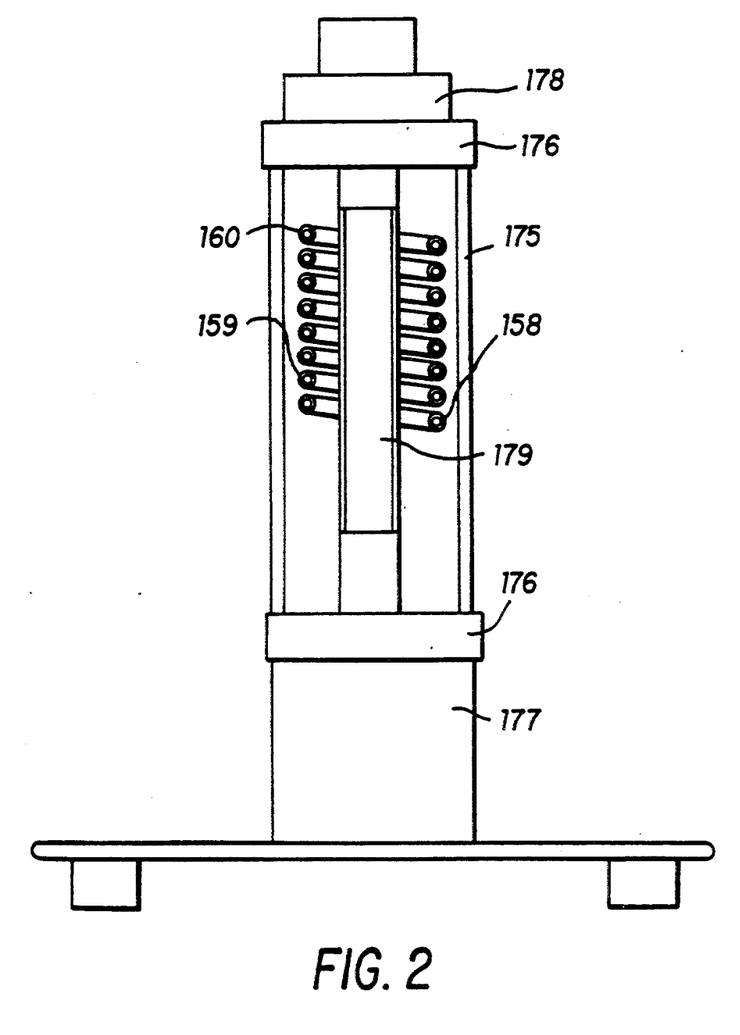
FIG. 2 is an elevational view, partly in section, of the exposure device of the apparatus of FIG. 1.

As illustrated in FIG. 2, the structure of irradiation device 150 includes a heat-resistant glass (e.g. PYREX) tube 159 wound helically around a cylindrical lamp 179. The irradiation device also includes an aluminum housing 175, a base section 177 with a fan and sleeves 176 above and below the cylindrical lamp 179 to position the lamp 179 centrally within aluminum housing 175. A vented cap portion 178 has vents for cooling air to flow out and a recess for receiving the top of lamp 179. As shown in FIG. 1, the lower end 158 and upper end 160 of tube portion 159 extend out through holes in aluminum housing 175.

Referring now to FIG. 3, a system is shown by which the present invention has been demonstrated in the Examples, but which system is less preferred to that of FIG. 1 for practise of the present invention. The flow cell 30 in FIG. 3 is identical to flow cell 30 of FIG. 1 except that valve 66 is shown in the analysis position (which is also used for flushing the sample pathway). Further description of FIG. 3 can be found in U.S. Ser. No. 257,553, and is incorporated herein by reference.

FIG. 3 represents a conventional blood gas instrument to which irradiation device 150 has been connected for purposes of demonstrating the present invention. Therefore calibration line 37 is connected to a first bubble chamber 39 (designated 152 in U.S. Pat. No. 4,361,539) which is fed by a first gas mixture in a first gas tank 41. A second calibration line (not shown, but referred to as 164 in U.S. Pat. No. 4,361,539) is connected from an inlet to valve 66 to a second bubble chamber 38 (designated 154 in that patent) which is fed by a second gas mixture in a second gas tank 40. The structure of such bubble chambers are illustrated in FIG. 3 of U.S. Pat. No. 4,361,539. For purposes of demonstrating the present invention, the instrument was calibrated prior to each measurement of irradiated calibrant by gas from first bubble chamber 39, and was also periodically calibrated by a two-point calibration, using both first and second bubble chambers 38 and 39. As described in U.S. Pat. No. 4,361,539, valve 66 is turned to one position to connect bubble chamber 39 to leg 62.

In the arrangement shown in FIG. 3, the sample valve 23 has been used to connect irradiation chamber 150 to the serpentine flow path through flow cell 30. It will be appreciated that a sample valve is already present in the Instrumentation Laboratory Model 1312 Blood Gas Instruments, but is used there to connect two different sample inlets to the sample preheater (typically a regular inlet for drawing 120 microliter samples, and a second inlet for drawing 65 microliter samples). In the system shown in FIG. 3, sample valve 23 can connect sample inlet line 24 either to line 22 (which goes to waste) or via line 162 to line 161. Line 163 also connects line 162 to valve 100 between line 98 and 102.

As with the system shown in FIG. 1, irradiation chamber 150 is connected in FIG. 3 so as to draw calibration liquid from either reservoir 151 or reservoir 152 through selector valve 153, line 154, intake valve 155, line 157 and exposed glass tube portion 158 into coil portion 159 of irradiation device 150. Once coil portion 159 was filled with liquid, valve 155 was turned to connect line 157 through line 156 to room air. By having line 157 connected to line 154 only when coil portion 159 was being filled with calibration liquid, air was introduced both ahead of and behind each aliquot of calibration liquid.

After exposure of the aliquot of calibration liquid in device 150, valves 156, 23 and 100 were turned (and valve 68 rotated to the position shown in FIG. 3 if not already there) so that aspiration pump 104 could apply vacuum to outlet portion 84 of the serpentine flow path through flow cell 30. Exposed calibration liquid in coil portion 159 was drawn into flow cell 30 through lines 161 and 162, valve 23, sample inlet line 24 and sample preheater 25. To obtain a valid measurement on fully exposed calibration liquid, any aliquots which had been in exposed tube portion 160 or line 161 during exposure should, during measurement, be in or above transverse passage 68 (and normally such aliquots were in outlet passage 84 or beyond). Any aliquot of treating liquid which had been in line 157 or tube portion 158 during the lastest exposure should be to the right of sample preheater 25 (i.e., in line 24, 162 or 161) at the time of analysis.

EXAMPLES

COMPARATIVE EXAMPLE 1

An aqueous solution containing 50 mM sulfuric acid, 0.75 mM potassium oxalate monohydrate and 0.25 mM ferric ammonium sulfate dodecahydrate was prepared and equilibrated with room air in the absence of light. Aliquots of this solution, each 300 microliters, were placed in a commercially available SUPRASIL quartz optical cuvette (Catalog Number 14-385-927B from Fisher Scientific Company) having an optical path length of 1.0 cm. The cuvette was sealed with a silicone rubber cap to limit the headspace above the solution to no more than 80 microliters. Different aliquots were irradiated for different lengths of time by placing the cuvette directly in front of a Pyrex glass-filtered xenon flash lamp (Model FX-193U lamp with a Model FY-714 trigger module operated by a Model PS302 power supply, all from EG&G Electro-optics; the power supply was externally triggered by a Model 175 universal programmer from EG&G PARC.) The lamp was operated at 275 Hertz with an average power of 16 Watts. Immediately after irradiation, each aliquot was run on an unmodified Instrumentation Laboratory Model 1312 blood gas instrument, as a sample drawn into the main sample port.

Values for pCO2 and pO2 given by the instrument for two replications of these aliquots were recorded and are tabulated in Table I.

TABLE I

| Irradiation Time in seconds | Average $pCO_2$ in mm Hg | Average $pO_2$ in mm Hg |
| --- | --- | --- |
| 0 | 7.5 | 197 |
| 30 | 17.2 | 85 |
| 60 | 21.6 | 36 |
| 90 | 27.0 | −2 |
| 120 | 31.1 | −2 |
| 150 | 32.6 | −2 |
| 180 | 34.0 | −1 |
| 240 | 34.9 | 6 |

An evaluation of this data shows the pCO2 values reaching a plateau within 120 seconds and the pO2 values declining to essentially 0 within 90 seconds. The small oxygen value after 180 seconds is believed to be caused by contamination.

These results show that a stoichiometric 3:1 molar ratio (oxalate to iron (III)) leads to oxygen consumption, but that the reaction is relatively slow (over 90 seconds to completion).

EXAMPLE 2

An aqueous solution was prepared and equilibrated as in Example 1, but now containing 50 mM sulfuric acid, 1.50 mM potassium oxalate monohydrate and 15.0 mM ferric ammonium sulfate dodecahydrate. Aliquots of 300 microliter volume were irradiated and immediately run on the Model 1312 blood gas instrument as in Example 1. Results of two replications are tabulated in Table 2.

TABLE 2

| Irradiation Time in seconds | Average $pCO_2$ in mm Hg | Average $pO_2$ in mm Hg |
| --- | --- | --- |
| 0 | 7.6 | 195 |
| 30 | 35.2 | 191 |
| 60 | 51.9 | 188 |
| 90 | 65.4 | 185 |
| 120 | 71.8 | 185 |
| 150 | 75.4 | 181 |
| 180 | 76.6 | 180 |
| 240 | 75.3 | 179 |

An evaluation of this data shows the pCO2 values reaching a plateau within 150 seconds and the pO2 values declining only about 8%. The molar ratio was 10:1 iron (III) to oxalate, a large excess of iron (III) over stoichiometry for ferrioxalate.

COMPARATIVE EXAMPLE 3

An aqueous solution containing 50 mM sulfuric acid, 0.68 mM potassium oxalate monohydrate and 13.5 mM ferric ammonium sulfate dodecahydrate was prepared and equilibrated with room air in the absence of light. The amber polyethylene container in which the solution was stored was connected to a modified Model 1312 blood gas instrument in the manner shown in FIG. 3. Using a personal computer to automatically regulate the various pumps shown in FIG. 3 and the circuits controlling the valves shown in FIG. 3, the aqueous solution was introduced into the irradiation chamber shown in FIG. 2. The programming of the personal computer caused irradiation device 150 to operate at an average power of 8 Watts for a variable length of time. Upon completion of the exposure, the aliquot of liquid then in irradiation device 150 was brought into the blood gas instrument as shown in FIG. 3 and run as a sample. Details of the fluidic cycle are described above in connection with FIG. 3. In particular, each 300 microliter aliquot of liquid was drawn from the amber polyethylene container into an exposure position in which its leading edge was in exposed tube portion 160. Then, after exposure, and with valve 155 turned to admit air through line 156 behind the aliquot, that leading edge was drawn through lines 161 and 24 into the serpentine path in the blood gas instrument and past the leg 80 of that path until it was sensed by position sensor 88.

Values of pCO2 and pO2 obtained for three replications of the various irradiation times are tabulated in Table III.

TABLE III

| Irradiation Time in seconds | Average $pCO_2$ in mm Hg | Average $pO_2$ in mm Hg |
| --- | --- | --- |
| 0 | 5.0 | 179 |
| 15 | 12.4 | 172 |
| 30 | 15.0 | 170 |

TABLE III-continued

| Irradiation Time in seconds | Average pCO2 in mm Hg | Average pO2 in mm Hg |
|---|---|---|
| 60 | 19.8 | 168 |
| 90 | 23.5 | 167 |
| 120 | 26.9 | 165 |
| 180 | 33.0 | 167 |

Iron (III) was in substantial molar excess (20:1 iron (III) to oxalate molar ratio). An evaluation of this data shows the pCO2 values approaching the plateau within 180 seconds and the pO2 values not declining significantly over that period. A higher power in irradiation device 150 would be expected to enable the plateau value of pCO2 to be reached more quickly, e.g., in sixty seconds or less.

COMPARATIVE EXAMPLE 4

An aqueous solution was prepared and equilibrated as in Example 3, but now containing 50 mM sulfuric acid, 1.35 mM potassium oxalate monohydrate and 1.35 mM ferric ammonium sulfate dodecahydrate. Aliquots of this solution were irradiated and run in the Model 1312 blood gas instrument as described in Example 3. Results are tabulated in Table IV.

TABLE IV

| Irradiation Time in seconds | Average pCO2 in mm Hg | Average pO2 in mm Hg |
|---|---|---|
| 0 | 7.0 | 176 |
| 15 | 19.8 | 156 |
| 30 | 27.9 | 136 |
| 60 | 37.1 | 106 |
| 90 | 42.4 | 78 |
| 120 | 49.2 | 50 |
| 150 | 53.5 | 35 |
| 180 | 55.8 | 26 |
| 210 | 55.2 | 27 |

An evaluation of this data shows the pCO2 values approaching the plateau within 180 seconds and the pO2 declining to a plateau within 180 seconds. Experiments performed after the filing of U.S. Ser. No. 257,553 in the mode of Comparative Example 1 suggest that, at this 1:1 molar ratio, even higher power may not suffice to reach plateau values of carbon dioxide partial pressure in 60 seconds.

EXAMPLES 5-27

The procedures of comparative Example 1 were followed for compositions having varying proportions of oxalate (as mM potassium oxalate) and iron (III) (as mM ferric ammonium sulfate) as indicated in Table V, below. Sulfuric acid was used at 500 mM in Examples 5 and 6 and at 50 mM in the other Examples. The plateau level of pCO2 and % reduction in pO2 observed were as indicated in Table V. The results of Examples 1-4 are also summarized in Table V.

TABLE V

| Example | Fe(III) mM | Oxalate mM | Ratio | pCO2 | % pO2 red |
|---|---|---|---|---|---|
| 1 | 0.25 | 0.75 | 1:3 | 35 | 100 |
| 2 | 15.0 | 1.5 | 10:1 | 75 | 8 |
| 3 | 13.5 | 0.68 | 20:1 | 33 | 7 |
| 4 | 1.35 | 1.35 | 1:1 | 55 | 85 |
| 5 | 15.0 | 0.75 | 20:1 | 37 | 10 |
| 6 | 27 | 1.35 | 20:1 | 46 | 7 |
| 7 | 0.25 | 5.0 | 1:20 | 35 | 100 |
| 8 | 0.25 | 50 | 1:200 | 39 | 95 |
| 9 | 0.25 | 100 | 1:400 | 39 | 95 |
| 10 | 0.25 | 500 | 1:2000 | 39 | 100 |
| 11 | 0.25 | 1000 | 1:4000 | 38 | 100 |
| 12 | 0.25 | 1800 | 1:7200 | 35 | 100 |
| 13 | 0.25 | 250 | 1:1000 | 40 | 100 |
| 14 | 32.5 | 0.65 | 50:1 | 34 | 4 |
| 15 | 65 | 0.65 | 100:1 | 35 | 4 |
| 16 | 0.25 | 1.25 | 1:5 | 33 | 100 |
| 17 | 0.25 | 2.5 | 1:10 | 34 | 100 |
| 18 | 0.25 | 5 | 1:20 | 34 | 100 |
| 19 | 0.20 | 20 | 1:100 | 36 | 100 |
| 20 | 0.20 | 40 | 1:200 | 37 | 96 |
| 21 | 0.20 | 60 | 1:300 | 35 | 98 |
| 22 | 0.20 | 60 | 1:300 | 37 | 99 |
| 23 | 0.20 | 80 | 1:400 | 39 | 95 |
| 24 | 0.25 | 250 | 1:1000 | 40 | 100 |
| 25 | 0.25 | 500 | 1:2000 | 40 | 100 |
| 26 | 0.25 | 1000 | 1:4000 | 38 | 100 |
| 27 | 0.25 | 1800 | 1:7200 | 36 | 100 |

Example 22 differed from Example 21 in having more sulfuric acid (0.75 in Example 22; 0.50 mM in Example 21) to lower the pH (1.28 in Example 22 and 1.78 in Example 21). The large amounts of potassium oxalate in Examples 22-27 may have raised the pH above the preferred 1.0 to 1.5 range.

These results demonstrate that iron (III)-excess compositions (e.g., in Examples 2, 3, 5, 6, 14 and 15) cause 10% or less reduction in oxygen partial pressure. Thus, these compositions can be used to calibrate an electrode array at high pO2 (above arterial blood values and near atmospheric values). Examples 2 and 6 show that these can be at high pCO2 value (75 and 46 torr, respectively). Examples 3, 14 and 15 show that these can be at lower pCO2 values as well (33-35 torr).

While many of the compositions showed complete or near-complete oxygen consumption at ratios from 1:1 (Example 4) to 1:7200 (Example 27), further work, described below, indicates the preferences for 1:5, 1:100 and even more oxalate-rich mixtures.

EXAMPLES 28-31

Stability

Compositions were prepared as described below and tested as in Example 1 before and after a period 21 or 34 days at 45° C. in brown glass bottles. The compositions, ratios, pCO2 plateau values and PO2 plateau values are summarized in Table VI.

TABLE VI

| Example | Day | Fe(III) mM | Oxalate mM | Ratio | pCO2 Plateau | pO2 Plateau |
|---|---|---|---|---|---|---|
| 28A | 0 | 0.25 | 0.75 | 1:3 | 43.7 | 15 |
| 28B | 34 | 0.25 | 0.75 | 1:3 | 41.4 | 17 |
| 29A | 0 | 0.20 | 20.0 | 1:100 | 36.0 | 0 |
| 29B | 34 | 0.20 | 20.0 | 1:100 | 37.2 | 14 |
| 30A | 0 | 0.20 | 80.0 | 1:400 | 35.8 | 15 |
| 30B | 21 | 0.20 | 80.0 | 1:400 | 36.8 | 16 |
| 31A | 13 | 15.0 | 1.5 | 10:1 | 77.9 | 172 |
| 31B | 34 | 15.0 | 1.5 | 10:1 | 73.2 | 169 |

These results show stable values for all four compositions, but somewhat better results for the largest oxalate excess (in Example 30) compared to lesser oxalate excesses (in Example 29) or stoichiometric amounts (Example 28). Example 31 shows good stability for an iron-rich composition (10:1 molar ratio) yielding high pCO2 values (around 75 torr) and high pO2 values (around 170 torr).

EXAMPLE 32

The procedures of Comparative Example 3 were repeated using a composition with 0.2 mM ferric ammonium sulfate and 0.2M (200 mM) potassium oxalate (a 1:1000 molar ratio). The results are shown in Table VII:

TABLE VII

Timed Results-Automated
0.2 mM Fe(III), 0.2 M Oxalate, 50 mM $H_2SO_4$

| Irradiation (sec) | $pCO_2$ (mm Hg) | $pO_2$ (mm Hg) |
| --- | --- | --- |
| 0 | 8.8 | 190 |
| 30 | 19.7 | 72 |
| 60 | 32.9 | 12 |
| 90 | 35.1 | 8 |
| 120 | 36.4 | 4 |
| 180 | 36.8 | 6 |
| 240 | 36.7 | 4 |

They show plateau values of $pCO_2$ (35-37 torr) being reached in 90 seconds and of $pO_2$ (4-8 torr) also in 90 seconds. Comparing Table VII to table IV, the $pO_2$ value can be seen to be lower and reached more quickly. It is these results (as well as the more extensive results summarized in Table V for ratios of 1:1 to 1:7200) that indicate that satisfactory values of $pCO_2$ and low $pO_2$ are achieved more rapidly with oxalate excesses; e.g., with at least 5:1 and preferably at least 100:1 molar ratios of oxalate to iron (III) rather than equimolar (1:1) or stoichiometric (3:1) ratios. See also Example 34 and Table IX, below.

COMPARATIVE EXAMPLE 33

Example 32 was repeated using a composition with 1.5 mM iron (III) and 1.5 mM oxalate. Similarly to Comparative Example 4, the results (displayed in Table VIII) show $pO_2$ values still declining at 120 seconds and eventually reaching a plateau value (27 torr) somewhat too high to be an ideal lower calibration value for a blood gas instrument.

TABLE VIII

Timed Results-Automated
1.5 mM Fe(III), 1.5 mM Oxalate, 50 mM $H_2SO_4$

| Irradiation (sec) | $pCO_2$ (mm Hg) | $pO_2$ (mm Hg) |
| --- | --- | --- |
| 0 | 7.0 | 176 |
| 15 | 19.8 | 156 |
| 30 | 27.9 | 136 |
| 60 | 37.1 | 106 |
| 90 | 42.4 | 78 |
| 120 | 49.2 | 50 |
| 150 | 53.5 | 37 |
| 180 | 55.8 | 26 |
| 210 | 55.2 | 27 |

GENERAL COMMENTS

In each of the above examples and in much of the description that precedes them, the actual measurement of $pCO_2$ and of $pO_2$ was electrochemical (with a Clark oxygen electrode and a Severinghaus carbon dioxide electrode). The use of the present solutions is not, however, so limited in that other modes of measurement, such as optical measurement of $pO_2$ and of $pCO_2$, can be employed. The irradiated calibration solution would be expected to perform satisfactorily with such non-electrode measuring elements.

Either a one-point calibration, a two-point calibration or another mode of comparison may be used. For example, the electronic circuitry can take the signal from the measurement of the exposed solution of Example 31 as the values for 75 mm Hg $pCO_2$ and for 170 mm Hg $pO_2$ and the values for the signal from the measurement of the exposed solution of Example 32 as the values for 36 mm Hg $pCO_2$ and for 5 mm Hg $pO_2$. From these two known values, functional relationships of signal to partial pressure can be established (e.g., linear relationships); and each signal generated when a measuring element measures a liquid sample can be converted to a partial pressure according to the respective functional relationship. Furthermore, one of the two sets of calibration values (e.g., the values for 75 mm Hg $pCO_2$ and for 170 mm Hg $pO_2$) can be stored over many sample measurements while the other set (e.g., the values for 36 mm Hg $pCO_2$ and for 5 mm Hg $pO_2$) can be reset by measuring an exposed aliquot of one calibration liquid prior to each sample measurement. In such cases, the $pO_2$ of the calibration liquid whose values are stored is preferably near 0 mm Hg.

EXAMPLE 34

Various compositions were prepared, similar to those of Comparative Example 1 and Examples 16–25 with either 0.20 or 0.25 mM iron (III) as indicated in Table IX, below, with iron (III) to oxalate molar ratios varying from 1:3 to 1:2000 as indicated in Table IX and 50 mM sulfuric acid. An aliquot of each was placed in the optical cuvette and exposed to light for time periods indicated in Table IX and tested on a Model 1312 Blood Gas Instrument, all as in Comparative Example 1. Exposure times were generally 0, 60, 120 and 180 seconds, with aliquots of many of the solutions also exposed for 30, 90, 150, 240 and/or 300 seconds. Results in measured $pO_2$ and measured $pCO_2$ are displayed in Table IX.

|  | $pCO_2$ | $pO_2$ | $pCO_2$ | $pO_2$ | $pCO_2$ | $pO_2$ | $pCO_2$ | $pO_2$ |
| --- | --- | --- | --- | --- | --- | --- | --- | --- |
| mM Fe(III) | 0.20 | | 0.25 | | 0.25 | | 0.25 | |
| Fe(III):Ox | 1:3 | | 1:5 | | 1:10 | | 1:20 | |
| Time (sec) | | | | | | | | |
| 0 | 7.0 | 184 | 7.2 | 199 | 7.3 | 201 | 7.6 | 200 |
| 30 | 27.3 | 99 | 16.8 | 76 | 17.2 | 82 | 18.4 | 73 |
| 60 | 34.2 | 48 | 21.4 | 21 | 22.7 | 20 | 24.9 | 6 |
| 90 | 41.3 | 14 | 27.5 | −1 | 28.7 | −1 | 31.8 | −1 |
| 120 | 43.7 | 15 | 30.8 | −1 | 32.1 | −1 | 33.6 | −1 |
| 150 | — | — | 31.9 | −1 | 33.1 | −1 | 34.4 | −1 |
| 180 | 41.3 | 16 | 33.0 | 0 | 34.0 | 0 | 35.2 | 5 |
| 240 | — | — | 33.9 | 9 | 34.1 | 1 | 35.6 | 10 |
| 300 | — | — | 34.3 | 10 | 35.1 | 10 | 35.7 | 11 |
| mM Fe(III) | 0.20 | | 0.20 | | 0.20 | | | |

-continued

| | $pCO_2$ | $pO_2$ | $pCO_2$ | $pO_2$ | $pCO_2$ | $pO_2$ | $pCO_2$ | $pO_2$ |
|---|---|---|---|---|---|---|---|---|
| Fe(III):Ox | 1:100 | | 1:200 | | 1:300 | | | |
| Time (sec) | | | | | | | | |
| 0 | 7.1 | 196 | 7.1 | 192 | 6.8 | 194 | | |
| 30 | — | — | — | — | 34.9 | 4 | | |
| 60 | 29.9 | 0 | 36.9 | 8 | 37.1 | 12 | | |
| 90 | — | — | — | — | 37.2 | 10 | | |
| 120 | 36.3 | 3 | 37.0 | 12 | 37.4 | 12 | | |
| 150 | — | — | — | — | — | — | | |
| 180 | — | — | — | — | 37.3 | 13 | | |
| mM Fe(III) | 0.25 | | 0.20 | | 0.25 | | 0.25 | |
| Fe(III):Ox | 1:400 | | 1:500 | | 1:1000 | | 1:2000 | |
| Time (sec) | | | | | | | | |
| 0 | 7.6 | 200 | 5.5 | 195 | 8.2 | 199 | 8.6 | 187 |
| 30 | 38.0 | 11 | 38.4 | 15 | 39.6 | 1 | 38.8 | 0 |
| 60 | 39.1 | 11 | 38.7 | 15 | 40.0 | 1 | 39.6 | 0 |
| 90 | 39.1 | 10 | 38.7 | 14 | 40.2 | 1 | 39.5 | 0 |
| 120 | 39.1 | 11 | 38.8 | 14 | 40.1 | 1 | 39.9 | 0 |
| 150 | — | — | — | — | — | — | — | — |
| 180 | 38.9 | 11 | — | — | 40.0 | 1 | 40.1 | 0 |
| 240 | 39.1 | 11 | — | — | 41.1 | 1 | — | — |

The plateau pO2 value was essentially zero in most cases, but was somewhat higher for 1:3, 1:200, 1:300, 1:400 and 1:500 ratios. After extended exposure periods, pO2 rose from the plauteau minimum (after 300 seconds with 1:10 and 1:20), probably due to air leakage in these isolated cases.

There is some pattern as to how quickly the plateaus were reached. For pCO2, the plateau was reached in 60 seconds or less for ratios from 1:200 through 1:2000, and in 90 seconds for 1:5, 1:10 and 1:20. Data at 1:100 are insufficient. For pO2, a flat plateau minimum was reached in 60 seconds or less of exposure for 1:300 through 1:2000 and in 90 seconds at 1:3, 1:5, 1:10 and 1:20. Data was insufficient at 1:100 and 1:200, but it appears that a minimum may have been reached in 60 seconds in these cases.

Based upon these results, formulations having a 1:100 molar ratio of iron (III) to oxalate, or richer in oxalate than that, appear to reach minimum oxygen values and a plateau of carbon dioxide values within 60 seconds under the test conditions, and are therefore preferred. Ratios of 1:5 to 1:100 are less preferred, because 90 seconds exposure was required. The formulation at 1:3 molar ratio required 90 seconds to reach an apparent plateau, but that plateau may have been less flat as to pCO2 and higher as to pO2 than the formulations from 1:5 to 1:100. The risk with such a stoichiometric formulation is that, if any ferrioxalate decomposes by less prevalent mechanisms, then some iron (III) may remain so as to introduce variability into the pCO2 and pO2 values; with oxalate excesses over iron (III), it can be expected that the oxygen consuming reaction will consume all of the iron (III) as well.

What is claimed is:

1. An aqueous solution having a pH of 0 to 5 and comprising 0.3 to 15 millimoles per liter oxalate and 1.5 to 200 millimoles per liter of iron (III); the molar ratio of iron (III) to oxalate being 5:1 to 100:1.

2. The aqueous solution of claim 1 wherein the pH is 0 to 2.

3. The aqueous solution of claim 2 wherein the molar ratio of iron (III) to oxalate is 10:1 to 50:1.

4. The aqueous solution of claim 3 wherein the oxalate concentration is 0.6 to 1.5 millimoles per liter and the iron (III) concentration is 6 to 75 millimoles per liter.

5. The aqueous solution of claim 2 wherein the oxalate concentration is 0.6 to 1.5 millimoles per liter.

6. An aqueous solution having a pH of 0 to 5 and comprising 0.2 to 5 millimoles per liter iron (III) and at least 1 millimole per liter oxalate; the molar ratio of oxalate to iron (III) being at least about 5:1.

7. The aqueous solution of claim 6 having a pH of 0 to 2.

8. The aqueous solution of claim 7 having 0.2 to 0.5 millimoles per liter iron (III).

9. The aqueous solution of claim 8 wherein the molar ratio of oxalate to iron (III) is at least about 100:1.

10. The aqueous solution of claim 8 wherein the molar ratio of oxalate to iron (III) is about 100:1 to about 2000:1.

11. The aqueous solution of claim 10 having 0.20 to 0.25 millimoles per liter iron (III).

12. The aqueous solution of claim 11 having a pH of 1.0 to 1.5.

13. The aqueous solution of claim 8 wherein the molar ratio of oxalate to iron (III) is about 300:1 to about 1000:1.

14. An aqueous solution having a pH of 0 to 5 and comprising 0.1 to 5 millimoles per liter iron (III) and at least 10 millimoles per liter oxalate; the molar ratio of oxalate to iron (III) being at least about 100:1.

15. The aqueous solution of claim 14 having a pH of 0 to 2.

16. The aqueous solution of claim 15 having 0.1 to 0.5 millimoles per liter iron (III).

17. The aqueous solution of claim 16 wherein the molar ratio of oxalate to iron (III) is about 100:1 to about 2000:1.

18. The aqueous solution of claim 16 wherein the molar ratio of oxalate to iron (III) is about 300:1 to about 1000:1.

19. The aqueous solution of claim 16 having a pH of 1.0 to 1.5.

* * * * *